United States Patent
Ledermann

(10) Patent No.: US 9,857,330 B2
(45) Date of Patent: Jan. 2, 2018

(54) METHOD AND DEVICE FOR DIAGNOSING THE AIR REFERENCE CHANNEL OF A BROADBAND LAMBDA PROBE

(71) Applicant: Robert Bosch GmbH, Stuttgart (DE)

(72) Inventor: Bernhard Ledermann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 334 days.

(21) Appl. No.: 14/438,167

(22) PCT Filed: Sep. 30, 2013

(86) PCT No.: PCT/EP2013/070319
§ 371 (c)(1),
(2) Date: Apr. 23, 2015

(87) PCT Pub. No.: WO2014/063903
PCT Pub. Date: May 1, 2014

(65) Prior Publication Data
US 2015/0276672 A1  Oct. 1, 2015

(30) Foreign Application Priority Data
Oct. 23, 2012 (DE) .......... 10 2012 219 282

(51) Int. Cl.
*G01N 27/409* (2006.01)
*G01N 27/417* (2006.01)
(Continued)

(52) U.S. Cl.
CPC ....... *G01N 27/4175* (2013.01); *G01N 27/409* (2013.01); *G01N 27/41* (2013.01);
(Continued)

(58) Field of Classification Search
CPC ............ G01N 27/406; G01N 27/4065; G01N 27/407–27/4072; G01N 27/409;
(Continued)

(56) References Cited

U.S. PATENT DOCUMENTS

| 5,494,557 A * | 2/1996 | Hotzel | G01N 27/4071 |
| | | | 204/425 |
| 6,818,111 B1 * | 11/2004 | Lenfers | G01N 27/4065 |
| | | | 204/406 |
| 7,461,536 B2 * | 12/2008 | Schnaibel | G01N 27/4175 |
| | | | 204/401 |

FOREIGN PATENT DOCUMENTS

| DE | 102008001697 | 11/2009 |
| DE | 102008002734 | 12/2009 |

(Continued)

OTHER PUBLICATIONS

The Bosch product information for the CJ135 Lambda probe interface IC, published Dec. 2010.*

(Continued)

*Primary Examiner* — Alexander Noguerola
(74) *Attorney, Agent, or Firm* — Norton Rose Fulbright US LLP; Gerard Messina

(57) ABSTRACT

A method is provided for diagnosing a reference channel of a broadband lambda probe that is used to determine an oxygen concentration in an exhaust gas, at least one sensor element having a pump cell and a Nernst cell being used; in one measurement mode, a regulated pumping current flowing through the pump cell to determine the oxygen concentration in the exhaust gas, and thus an exchange of oxygen ions between a measuring cell and the exhaust gas being achieved, and a lambda value in the measuring cell being regulated to a value of 1; the lambda value in the measuring cell being monitored through the Nernst cell, and the value of the pumping current required for that purpose being dependent on the oxygen concentration and thus on the lambda value of the exhaust gas to be determined.

14 Claims, 2 Drawing Sheets

(51) Int. Cl.
    *G01N 27/419*    (2006.01)
    *G01N 27/41*    (2006.01)
    *G01N 33/00*    (2006.01)
    *G01N 27/406*    (2006.01)

(52) U.S. Cl.
    CPC ....... *G01N 27/419* (2013.01); *G01N 27/4065* (2013.01); *G01N 33/0006* (2013.01)

(58) Field of Classification Search
    CPC ............... G01N 27/41; G01N 33/0006; G01N 33/0008; G01N 33/0037; G01N 33/0004
    See application file for complete search history.

(56) References Cited

FOREIGN PATENT DOCUMENTS

| | | |
|---|---|---|
| DE | 102009045445 | 4/2011 |
| DE | 102010000663 | 7/2011 |
| DE | 102010039188 | 2/2012 |
| EP | 0833148 | 4/1998 |
| EP | 0964246 | 12/1999 |
| JP | 2006-509151 A | 3/2006 |
| WO | 00/37930 A1 | 6/2000 |
| WO | WO2004/053475 | 6/2004 |
| WO | 2012/007238 A1 | 1/2012 |

OTHER PUBLICATIONS

International Search Report for PCT/EP2013/070319, dated Jan. 2, 2014.

\* cited by examiner

METHOD AND DEVICE FOR DIAGNOSING THE AIR REFERENCE CHANNEL OF A BROADBAND LAMBDA PROBE

FIELD OF THE INVENTION

The present invention relates to a method for diagnosing a reference channel of a broadband lambda probe that is used to determine an oxygen concentration in an exhaust gas, at least one sensor element having a pump cell and a Nernst cell being used; in one measurement mode, a regulated pumping current flowing through the pump cell to determine the oxygen concentration, and thus an exchange of oxygen ions between a measuring cell and the exhaust gas being achieved, and a lambda value in the measuring cell being regulated to a value of 1; the lambda value in the measuring cell being monitored through the Nernst cell, the value of the pumping current required for that purpose being dependent on the oxygen concentration and thus on the lambda value of the exhaust gas to be determined, the sensor element, together with the electrodes thereof, being connected to a control unit for controlling and analyzing the broadband lambda probe; besides the measurement mode, at least one diagnostic mode also being provided.

The present invention also relates to a corresponding device for implementing the inventive method.

BACKGROUND INFORMATION

Lambda probes are used in the exhaust branch of internal combustion engines, for example, for measuring the oxygen concentration of the exhaust gas, in order to control the preparation of the fuel-air mixture of the internal combustion engine. They utilize the property of a solid electrolyte composed of a zirconium dioxide ceramic, which, above a temperature of approximately 300° C., is permeable to oxygen ions. Platinum electrodes are mounted on at least two sides of the solid electrolyte. If one of the sides is exposed to an exhaust gas having decreased partial oxygen pressure, and the other side to a reference gas, for example air, oxygen ions diffuse through the solid electrolyte. The resulting potential difference between the two electrodes of such a concentration cell is described by the Nernst equation and can be used to determine the lambda value of the exhaust gas within a narrow window around lambda=1. The lambda value represents the existing air-fuel ratio relative to a stoichiometric air-fuel ratio.

Oxygen ions can be pumped through the solid electrolyte in response to application of an external voltage to the electrodes. This property is utilized in what are commonly known as broadband lambda probes to determine the lambda value within a broad range from lean to rich exhaust gas. To this end, an electrode, the external pump electrode, faces the exhaust gas. As the inner pump electrode, the second electrode communicates via a diffusion barrier with the exhaust gas. The second electrode can be configured in a measuring cell in the solid electrolyte that communicates with the exhaust gas through a diffusion channel and the diffusion barrier. In one alternative configuration, both electrodes are disposed on the side of the solid electrolyte facing the exhaust gas, the inner pump electrode being covered by an applied diffusion barrier layer.

The outer pump electrode, the inner pump electrode and the solid electrolyte disposed therebetween form what it commonly known as a pump cell. In response to the application of a voltage, oxygen ions are transported from the inner pump electrode to the outer pump electrode. If the voltage is high enough, a limiting current is reached that is determined by the oxygen diffusion through the diffusion barrier. The oxygen diffusion, and thus the limiting current measured to determine the lambda value, are directly dependent on the partial oxygen pressure in the exhaust gas, as well as on the diffusion properties of the diffusion barrier. The known diffusion properties of the diffusion barrier make it possible for the lambda of the exhaust gas to be determined from the limiting current.

Another structure known as a two-cell broadband lambda probe is formed from a combination of a pump cell and a concentration cell. The outer pump electrode faces the exhaust gas, and the inner pump electrode is configured in a measuring cell that communicates with the exhaust gas through the diffusion barrier. In addition, a first electrode of the concentration cell, referred to as measuring cell, is located in the measuring cell. As a second electrode of the concentration cell, a reference electrode is mounted on the solid electrolyte in a separate reference channel. The reference channel is filled through an external opening with a reference gas having a defined oxygen concentration, preferably with air.

In the case of such a two-cell broadband lambda probe, the pump cell pumps oxygen ions in or out to adjust the lambda value in the measuring cell to a lambda of preferably 1. To this end, the lambda value in the measuring cell is measured via the concentration cell and, by appropriately regulating the pumping current, regulated by the pump cell to $\lambda=1$. The pumping current required for that purpose is dependent on the oxygen quantity diffusing through the diffusion barrier into the measuring cell, and thus on the lambda of the exhaust gas, and the diffusion properties of the diffusion barrier. When the properties of the diffusion barrier are known, the lambda of the exhaust gas can be determined from the pumping current.

The diffusion properties of the diffusion barriers are subject to a substantial manufacturing variance. Therefore, the individual diffusion properties must be taken into account during analysis of the broadband lambda probe signals.

German Published Patent Application No. 10 2008 002 734 A1 describes an example of a broadband lambda probe.

German Published Patent Application No. 10 2010 000 663 A1, for example, discusses devices used as evaluation and control units for operating a broadband lambda probe. The fundamental idea, the structure and the basic function of the control unit described in this publication essentially correspond to the evaluation and control unit discussed in German Published Patent Application No. 10 2008 001 697 A1 of the Applicant. The control unit is designed as an ASIC and is known by the name CJ 125 or CJ 135 (see Product Information of the Applicant entitled "CJ135—Lambda Probe Interface IC").

German Published Patent Application No. 10 2010 039 188 A1 describes a method for sensing at least one property of a gas in a measuring cell, in particular for identifying a component of the gas. The method provides for using at least one sensor element having at least one cell. The cell has at least one first electrode, at least one second electrode, and at least one solid electrolyte through which the first electrode and the second electrode communicate with one another. The first electrode is able to receive gas from the measuring cell. The second electrode communicates with at least one reference gas cell that is adapted for storing a volume of a component of the gas. The method encompasses at least two operating modes:

at least one measurement mode; in the measurement mode, the cell being operated as a pump cell, and the property being inferred from at least one pumping current through the pump cell;

and at least one diagnostic mode, a storage capacity of the reference gas cell being examined in the diagnostic mode, a measured quantity influenced by at least one Nernst potential applied to the cell being recorded, and the storage capacity being inferred from the measured quantity.

For the operating principle thereof, a good portion of the lambda probes that are presently commercially available requires what is commonly known as an air reference (actually oxygen reference), that has the characteristic that the oxygen concentration of this air reference is 21% oxygen or higher. Certain inherent risks are associated with all of the methods that utilize this air reference since it does not contain enough oxygen, respectively is "contaminated" by elements where oxygen has a negative valence. This erroneous reference results in a displacement of the lambda characteristic curve and, as a logical consequence, in a faulty lambda determination, and sometimes in unwanted error entries in the software of the engine control unit. It is usually not possible to diagnose the air reference in conventional evaluation circuits, and allowances must be made for the residual risk described above.

SUMMARY

It is, therefore, an object of the present invention to provide a method which will make it possible for a simple and rapid diagnosis of the air reference described above to be implemented by broadband lambda probes.

It is also an object of the present invention to provide a corresponding device for implementing the method.

In terms of the method, the object of the present invention is achieved in that the pumping-current control circuit is switched over during the diagnostic mode, and the quality of an air reference in the reference channel is diagnosed via a voltage measurement. The method permits diagnosis of a faulty reference channel in the sensor element, thereby making it possible for a potentially incorrect lambda value to be avoided, and thereby enhancing the performance reliability of a lambda control for an internal combustion engine and assisting in avoiding pollutant emissions.

It is provided that the pumping-current control circuit be modified to change the oxygen concentrations in the sensor element in a way that makes possible a comparison measurement between two sites having high oxygen concentration. If a measuring result is obtained that is to be interpreted as an erroneous reference, this may consequently result in a plurality of scenarios. On the one hand, using a consistently high reference pumping current, it may be attempted to clean the air reference and to fill the same with oxygen. On the other hand, an error entry may indicate that it is absolutely necessary to replace an analyzer probe.

One preferred variant of the method provides that a maximum possible negative pumping current be adjusted for the diagnosis. This permits filling of the measuring cell with oxygen ions at a pressure above atmospheric. After only a brief time (typically after only <250 ms), this high oxygen partial pressure leads to a static state where all newly introduced oxygen ions are equalized via diffusion and flow through a diffusion barrier into the exhaust gas. Once the steady state is reached, the potential measurement mentioned at the outset may be implemented, without any changes as a function of time disturbing the same.

In addition, this may also be achieved by a request for a negative control voltage to be applied to the Nernst cell.

During the diagnostic phase, in which the thereby adjusting Nernst potential reaches a steady-state value, it is provided that it be analyzed; and an intact reference channel having an intact air reference is assumed if there is a Nernst potential of +50 mV to +150 mV; and a faulty air reference is assumed if, in comparison thereto, a thereby adjusting potential is lower or negative. This may be readily monitored using appropriate comparators.

One variant of the method provides that, in response to recognition of a fault, the request be made to connect the sensor element in order to intensively fill the reference channel with air, respectively oxygen, while the measured lambda value may be characterized as invalid in immediate temporal proximity to the diagnostic phase. The sensor element may consequently be at least partially regenerated, respectively "decontaminated."

If the measured Nernst potential is checked for plausibility, in particular within the range from 0 to 500 mV, an especially substantial reliability of diagnosis is obtained through further measures.

Due to the quite short diagnosis time of maximally one second, typically of approximately 0.5 seconds, the lambda measurement is only briefly interrupted, thereby continuing to enable an exhaust gas monitoring virtually without interruptions.

The diagnosis method including the previously mentioned method variants thereof is preferably carried out at the beginning of the service life of a broadband lambda probe and/or at specific intervals during the lifetime thereof. Thus, at the beginning of the service life, it is possible to discern whether the exhaust gas analyzer probe was stored too long or improperly. A use during the lifetime thereof advantageously permits recognition of aging or mechanical damage. Thus, temporarily "contaminated" analyzer probes may be regenerated before the lambda signal thereof is used. This may prevent incorrect secondary faults, which are difficult to identify, in the case of functionalities that utilize the lambda signal.

It is also advantageous that the diagnosis merely needs to be performed once during a driving cycle, in particular at the beginning or the end thereof.

In terms of the device, the object of the present invention is achieved in that the control unit has devices for implementing the method including the previously described method variants thereof, in particular switchover devices for changing a regulation of the pumping current through the pump cell, as well as comparators for analyzing a Nernst potential across the Nernst cell. The control unit may at least partially be an integral part of a higher-level engine management of an internal combustion engine. The functionality may be configured to be at least partially or completely software-based, so that, in particular, an adaptation is readily accomplished.

If, as provided by an especially preferred device variant, the control unit has a CJ 135 ASIC module, relatively little outlay is required for the practical application of the diagnosis method since this module already features corresponding, comprehensive setting options for undertaking the switchovers that must be carried out in comparison to normal operation.

DETAILED DESCRIPTION

Figure 1:
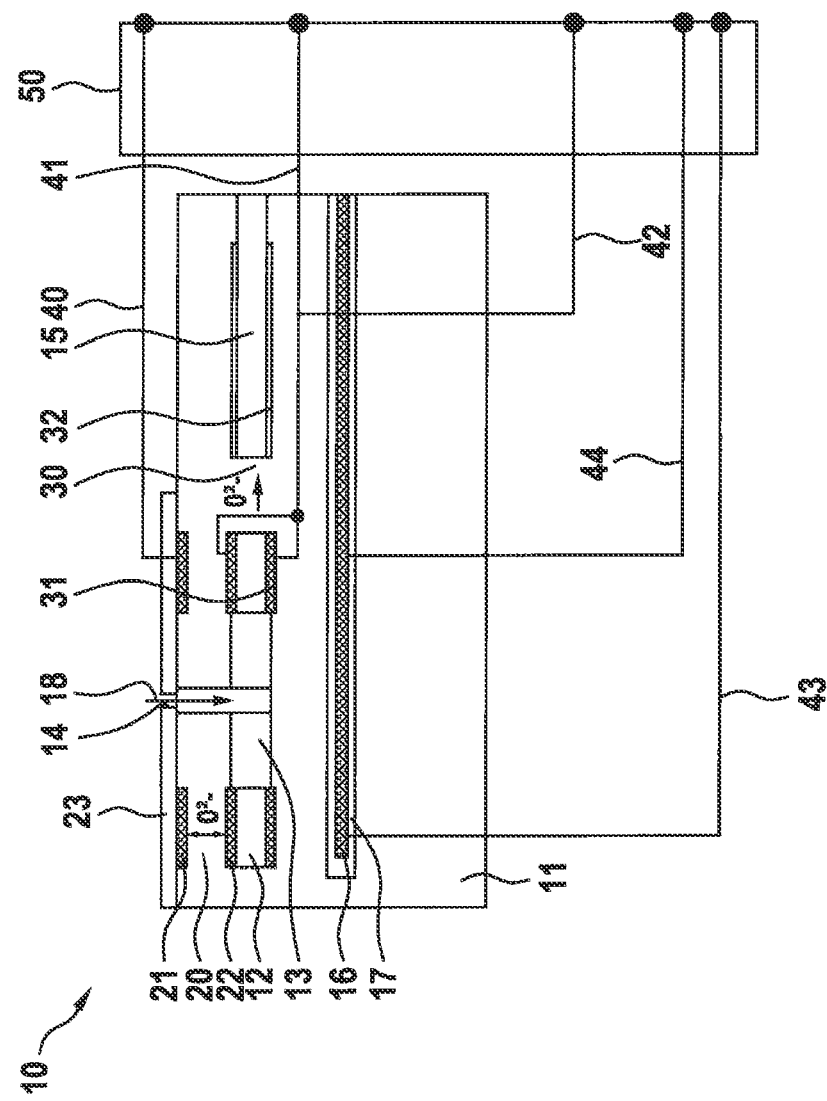
FIG. 1 shows, in a schematic representation, a sensor element of a two-cell broadband lambda probe having a connector housing.

FIG. 1 schematically shows a sensor element 10 of a planar, two-cell broadband lambda probe for determining a lambda value of an exhaust gas 18, that has a connector housing 50. Sensor element 10 is essentially constructed from a solid electrolyte 11. It contains a pump cell 20, a Nernst cell 30, and a heating element 16. Solid electrolyte 11 is shown in the representation as a homogeneous body of oxygen ion-conducting zirconium dioxide. In structure, however, it may be constituted of a plurality of solid electrolyte layers.

Pump cell 20 is composed of an outer pump electrode 21 and an inner pump electrode 22 configured in a measuring cell 12. Outer pump electrode 21, covered by a protective layer 23, is exposed to exhaust gas 18 of an internal combustion engine. Outer pump electrode 21 and inner pump electrode 22 are annularly configured about a diffusion channel 14. Diffusion channel 14 conveys the exhaust gas via a diffusion barrier 13 to measuring cell 12.

Located on the side of measuring cell 12 opposite inner pump electrode 22 is a measuring electrode 31. Together with a reference electrode 32 located in a reference channel 15 and solid electrolyte 11 disposed therebetween, measuring electrode 31 forms Nernst cell 30 or the concentration cell. Reference channel 15 is filled with an air-permeable material and is open to the ambient air as reference gas. In the case of a pumped reference, reference channel 15 may also be completely or substantially closed and, for example, be filled with zirconium dioxide. Reference channel 15 represents an air reference or also an oxygen reference.

Heating element 16 is electrically isolated from solid electrolyte 11 by an insulation material 17.

Outer pump electrode 21 is linked via a connection APE 40 to connector housing 50. Inner pump electrode 22 and measuring electrode 31 are connected in parallel and are coupled via a shared connection IPN 41 to connector housing 50. Reference electrode 32 is coupled via a connection RE 42, and heating element 16 via a first heating connection 43 and a second heating connection 44 to connector housing 50.

The electrodes, i.e., inner and outer pump electrode 21, 22, reference electrode 32 and measuring electrode 31 are manufactured from platinum.

During operation of the broadband lambda probe, exhaust gas diffuses via diffusion channel 14 and diffusion barrier 13 into measuring cell 12. Via Nernst cell 30, the lambda value in measuring cell 12 is determined by measuring the Nernst potential between measuring electrode 31 and reference electrode 32. Nernst cell 30 makes it possible to determine the lambda within a narrow measurement window around lambda=1. Applying a suitably polarized voltage between outer and inner pump electrode 21, 22 allows oxygen ions to be pumped through solid electrolyte 11 from the exhaust gas in measuring cell 12 or from measuring cell 12 to the exhaust gas.

Nernst cell 30 is regulated to a potential of 450 my during the operation using a control unit, which may be a CJ 135 ASIC, for example, as described in German Published Patent Application No. 10 2008 001 697 A1, utilizing a reference pumping current, so that measuring cell 12 (lambda 1 cavity) is to be regarded as essentially oxygen-free within the lambda probe.

This is accomplished by applying a current source to pump cell 20. By suitably regulating pumping current 102 flowing between pump electrodes 21, 22 (see FIG. 2) and thus the exchange of oxygen ions between measuring cell 12 and the exhaust gas, the lambda value in measuring cell 12 is regulated to a value of 1. The lambda value in measuring cell 12 is monitored in the process by Nernst cell 30. The value of the pumping current required for that purpose is dependent on the oxygen concentration and thus on the lambda value of the exhaust gas to be determined, as well as on the diffusion properties of diffusion barrier 13. An essential condition for the functioning of the design is that a chamber having a very high oxygen concentration, the air reference, be made available by the reference pumping current mentioned above.

If this air reference, respectively oxygen reference is not present, applied pumping current 102 (see FIG. 2) is no longer to be considered as a valid measure of the oxygen concentration of exhaust gas 18 in the sense of the definition of an analyzer probe.

During diagnosis of the air reference, the control unit (for example, CJ 135 ASIC) may be induced in the diagnosis time period to adjust a maximum negative pumping current 102 (see FIG. 2) that fills measuring cell 12 (lambda 1 cavity) with oxygen ions at a pressure above atmospheric. This may be on the order of −10 mA to −15 mA, for example, in this phase. This may be accomplished via a request for a negative control voltage at Nernst cell 30 or by requesting the pumping current operation set in the control unit.

The oxygen pressure above atmospheric described above (high partial oxygen pressure) leads after a brief time to a static state where all newly introduced oxygen ions are equalized via diffusion and flow through diffusion barrier 13 into exhaust gas 18.

Figure 2:
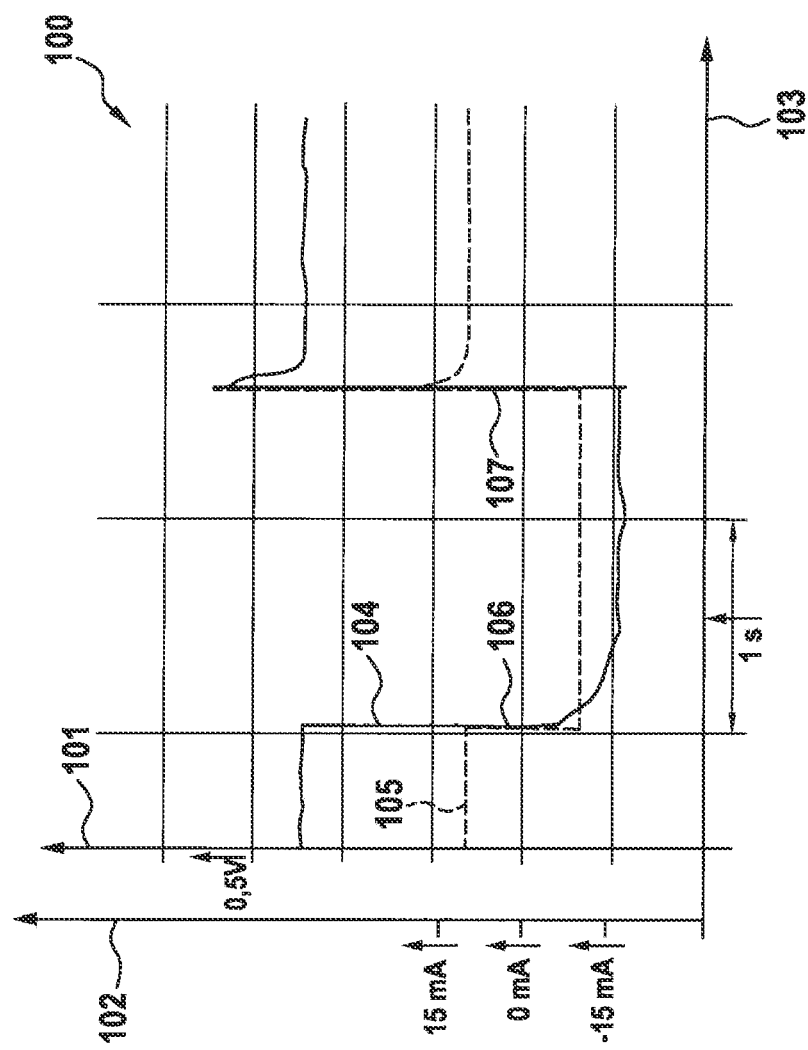
FIG. 2 shows a signal characteristic diagram for a Nernst potential and a pumping current.

FIG. 2 shows a signal characteristic diagram 100 for a Nernst potential curve 104 and a pumping current curve 105, the abscissa indicating time 103 and the ordinate the level of Nernst potential 101 and of pumping current 102.

Assuming a constantly regulated Nernst potential 101 of 450 mV along with a corresponding pumping current 102, a new static state is reached at a first slope 106 within approximately 250 ms in accordance with the measure described above. Between measuring cell 12 (lambda 1 cavity) and the air reference, a Nernst potential 101 is generated that is within the range of approximately +100 mV, since the partial oxygen pressure in the air reference is even higher than in measuring cell 12 that is now filled with oxygen. This is near +450 mV during normal operation.

If a distinctly negative potential is generated, then a faulty air reference may be assumed, and, in the case that this should actually be functional, an analyzer probe error is recognized, or a reaction for intensive filling of the air reference is requested, while the lambda signal is to be regarded as invalid.

As shown by a second slope 107 in Nernst potential curve 104, respectively in pumping current curve 105, it takes only approximately 200 ms to switch back into normal operation until pumping current 102 again indicates the correct value, and Nernst potential 101 is again adjusted to and maintained at a value of 450 mV. Altogether, the duration of a diagnosis cycle resides within the range of approximately one second and less (typically <500 ms). There is no need to perform the diagnosis more frequently than once per driving cycle. A possible time for the diagnosis is the beginning or end of a vehicle's driving operation, for example.

What is claimed is:

1. A method for diagnosing a reference channel of a broadband lambda probe that is used to determine an oxygen concentration in an exhaust gas, at least one sensor element having a pump cell and a Nernst cell, comprising:
in one measurement mode, causing a regulated pumping current to flow through the pump cell to determine the oxygen concentration in the exhaust gas, an exchange of oxygen ions between a measuring cell and the exhaust gas being achieved;
regulating by the measuring cell a lambda value in the measuring cell to a value of 1;
monitoring the lambda value in the measuring cell through the Nernst cell, a value of the pumping current required for the regulating being dependent on the oxygen concentration and on the lambda value of the exhaust gas, the sensor element and electrodes thereof being connected to a pumping-current control circuit for controlling and analyzing the broadband lambda probe; and
providing at least one diagnostic mode, wherein the pumping-current control circuit is switched over during the diagnostic mode, and a quality of an air reference in a reference channel is diagnosed via a voltage measurement, wherein the diagnosis is performed within a diagnosis time period of one second.

2. The method as recited in claim 1, wherein a highly negative pumping current is adjusted for a diagnosis.

3. The method as recited in claim 1, wherein a request for a negative control voltage is applied to the Nernst cell.

4. The method as recited in claim 1, wherein the method is carried out at at least one of a beginning of a service life of the broadband lambda probe and at specific intervals during a lifetime thereof.

5. The method as recited in claim 1, wherein the diagnosis is performed once during a driving cycle.

6. The method as recited in claim 1, wherein the diagnosis is performed once at one of a beginning and an end of a driving cycle.

7. A method for diagnosing a reference channel of a broadband lambda probe that is used to determine an oxygen concentration in an exhaust gas, at least one sensor element having a pump cell and a Nernst cell, comprising:
in one measurement mode, causing a regulated pumping current to flow through the pump cell to determine the oxygen concentration in the exhaust gas, an exchange of oxygen ions between a measuring cell and the exhaust gas being achieved;
regulating by the measuring cell a lambda value in the measuring cell to a value of 1;
monitoring the lambda value in the measuring cell through the Nernst cell, a value of the pumping current required for the regulating being dependent on the oxygen concentration and on the lambda value of the exhaust gas, the sensor element and electrodes thereof being connected to a pumping-current control circuit for controlling and analyzing the broadband lambda probe;
providing at least one diagnostic mode, wherein the pumping-current control circuit is switched over during the diagnostic mode, and a quality of an air reference in a reference channel is diagnosed via a voltage measurement; and modifying the pumping-current control circuit to allow oxygen concentrations in the sensor element to be changed in a way that makes possible a comparison measurement between two sites having high oxygen concentration.

8. A method for diagnosing a reference channel of a broadband lambda probe that is used to determine an oxygen concentration in an exhaust gas, at least one sensor element having a pump cell and a Nernst cell, comprising:
in one measurement mode, causing a regulated pumping current to flow through the pump cell to determine the oxygen concentration in the exhaust gas, an exchange of oxygen ions between a measuring cell and the exhaust gas being achieved;
regulating by the measuring cell a lambda value in the measuring cell to a value of 1;
monitoring the lambda value in the measuring cell through the Nernst cell, a value of the pumping current required for the regulating being dependent on the oxygen concentration and on the lambda value of the exhaust gas, the sensor element and electrodes thereof being connected to a pumping-current control circuit for controlling and analyzing the broadband lambda probe;
providing at least one diagnostic mode, wherein the pumping-current control circuit is switched over during the diagnostic mode, and a quality of an air reference in a reference channel is diagnosed via a voltage measurement; and
during the diagnostic mode, adjusting a Nernst potential to a virtually steady-state value;
after reaching the steady-state value, analyzing the Nernst potential, wherein:
if there is a Nernst potential of 0 to 500 mV, an intact reference channel having an intact air reference is assumed, and
in comparison thereto, if a thereby adjusting potential is lower or negative, a faulty air reference is assumed.

9. The method as recited in claim 8, wherein, in response to recognition of a fault, a request is made to connect the sensor element in order to intensively fill the reference channel with air while the measured lambda value is characterized as invalid in immediate temporal proximity to the diagnostic mode.

10. The method as recited in claim 8, wherein the Nernst potential is checked for plausibility through a further measure.

11. The method as recited in claim 10, wherein the Nernst potential is checked within a range from +50 mV to +150 mV.

12. A device for diagnosing a reference channel of a broadband lambda probe used for determining an oxygen concentration in an exhaust gas; at least one sensor element having a pump cell and a Nernst cell being provided, the device comprising:
a control unit connected to electrodes of the sensor element, the control unit being configured for controlling and analyzing the broadband lambda probe, wherein the control unit includes devices for implementing a method, comprising:
in one measurement mode, causing a regulated pumping current to flow through the pump cell to determine the oxygen concentration in the exhaust gas, an exchange of oxygen ions between a measuring cell and the exhaust gas being achieved;
regulating by the measuring cell a lambda value in the measuring cell to a value of 1;
monitoring the lambda value in the measuring cell through the Nernst cell, a value of the pumping current required for the regulating being dependent on the oxygen concentration and on the lambda value of the exhaust gas, the sensor element and electrodes thereof being connected to a pumping-current control circuit for controlling and analyzing the broadband lambda probe; and providing at least one diagnostic mode, wherein the pumping-current control circuit is switched over during the diagnostic mode, and a quality of an air reference in a reference channel is diagnosed via a voltage measurement, wherein the diagnosis is performed within a diagnosis time period of one second.

13. The device as recited in claim 12, wherein the devices for implementing the method includes:

switchover devices for changing a regulation of a pumping current through the pump cell, and comparators for analyzing a Nernst potential across the Nernst cell.

14. The device as recited in claim 12, wherein the control unit has a CJ 135 ASIC module.

* * * * *